United States Patent [19]

Conlon et al.

[11] Patent Number: 4,914,719
[45] Date of Patent: Apr. 3, 1990

[54] MULTIPLE COMPONENT GAS ANALYZER

[75] Inventors: Brendan Conlon, Elm Grove; James Dittmar, Waukesha, both of Wis.

[73] Assignee: Criticare Systems, Inc., Waukesha, Wis.

[21] Appl. No.: 321,897

[22] Filed: Mar. 10, 1989

[51] Int. Cl.$^4$ .............................. G01N 21/61
[52] U.S. Cl. ...................... 250/339; 250/343
[58] Field of Search .................. 250/343, 339

[56] References Cited

U.S. PATENT DOCUMENTS

| | | | |
|---|---|---|---|
| 3,793,525 | 2/1974 | Burch et al. | 250/343 |
| 3,811,776 | 5/1974 | Blau, Jr. | 356/51 |
| 4,480,190 | 10/1984 | Burough et al. | 250/343 |
| 4,578,762 | 3/1986 | Wong | 364/497 |
| 4,694,173 | 9/1987 | Wong | 250/343 |
| 4,771,176 | 9/1988 | Schiefer et al. | 250/339 |
| 4,801,805 | 1/1989 | Butler et al. | 250/343 |

OTHER PUBLICATIONS

V. V. Korloev, E. F. Timofeev and N. T. Shokina, "Filter—Type Analyzer for Continuous Impurity Monitoring for Flowing Titanium Tetrachloride," Translated from Zhurnal Prikladnoi Spektroskopii, vol. 22, No. 1 (Jan. 1975) pp. 148-152.

Primary Examiner—Constantine Hannaher
Attorney, Agent, or Firm—Willian Brinks Olds Hofer Gilson & Lione

[57] ABSTRACT

A gas multiple component analyzer includes an infrared source that passes at least one measuring beam through a sample cell that contains the gas to be analyzed. Three measuring signals are generated in response to the measuring beam, and each is indicative of optical energy from the source transmitted through the sample cell in a respective optical region characterized by a respective optical center wave-length and a respective band pass. The three measuring signals are algebraically combined to automatically determine which of the three end gases is present in the sample cell in the greatest concentration, and the concentration thereof. The disclosed system measures concentration of three separate gases having overlapping absorption spectra.

14 Claims, 8 Drawing Sheets

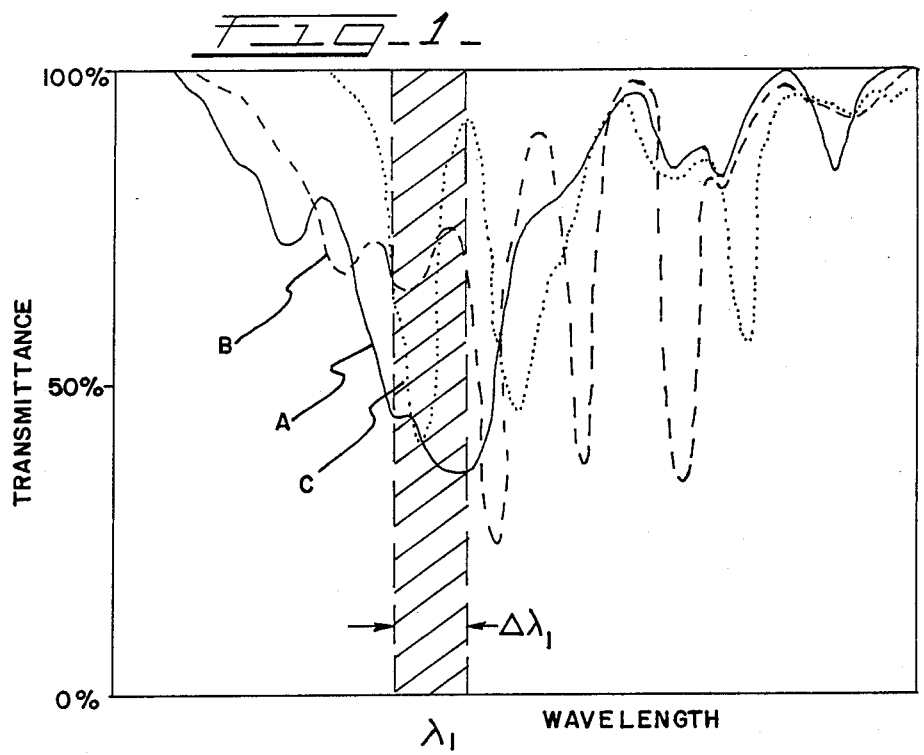
FIG_1_
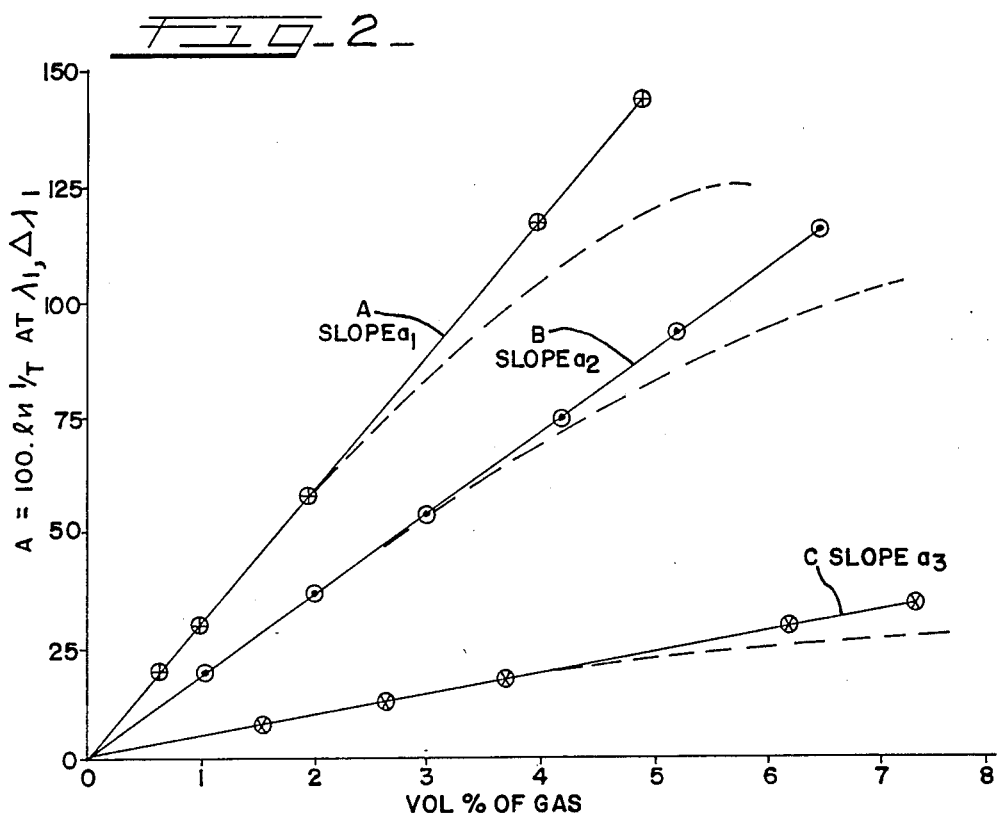
FIG_2_

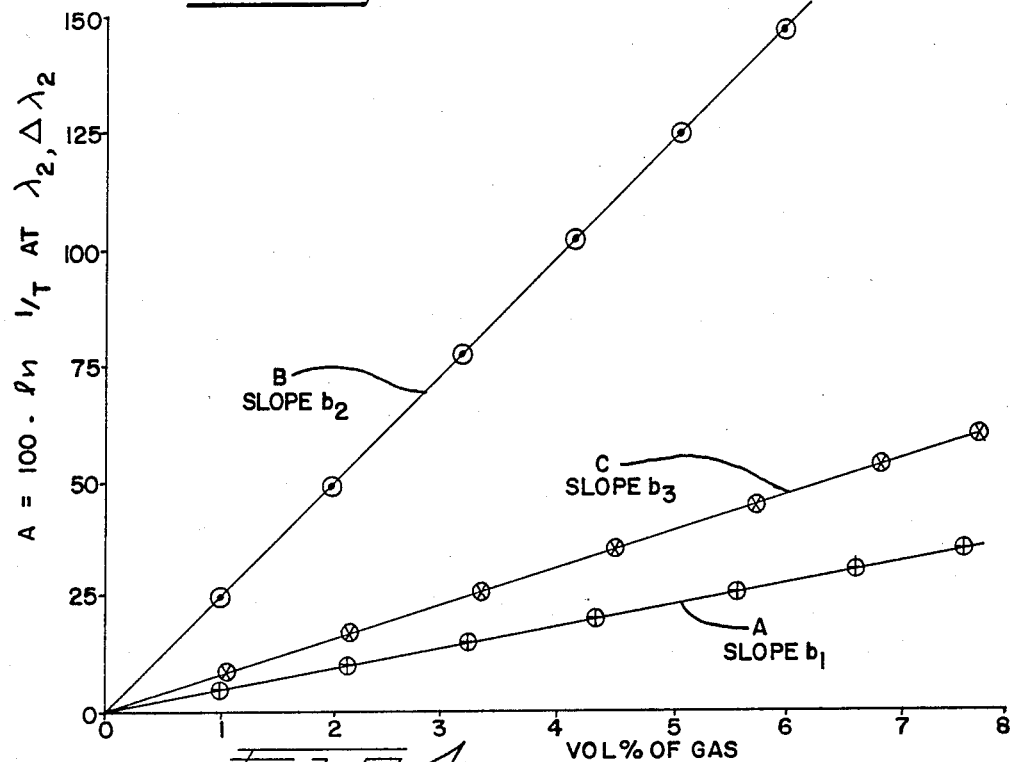
FIG-3-
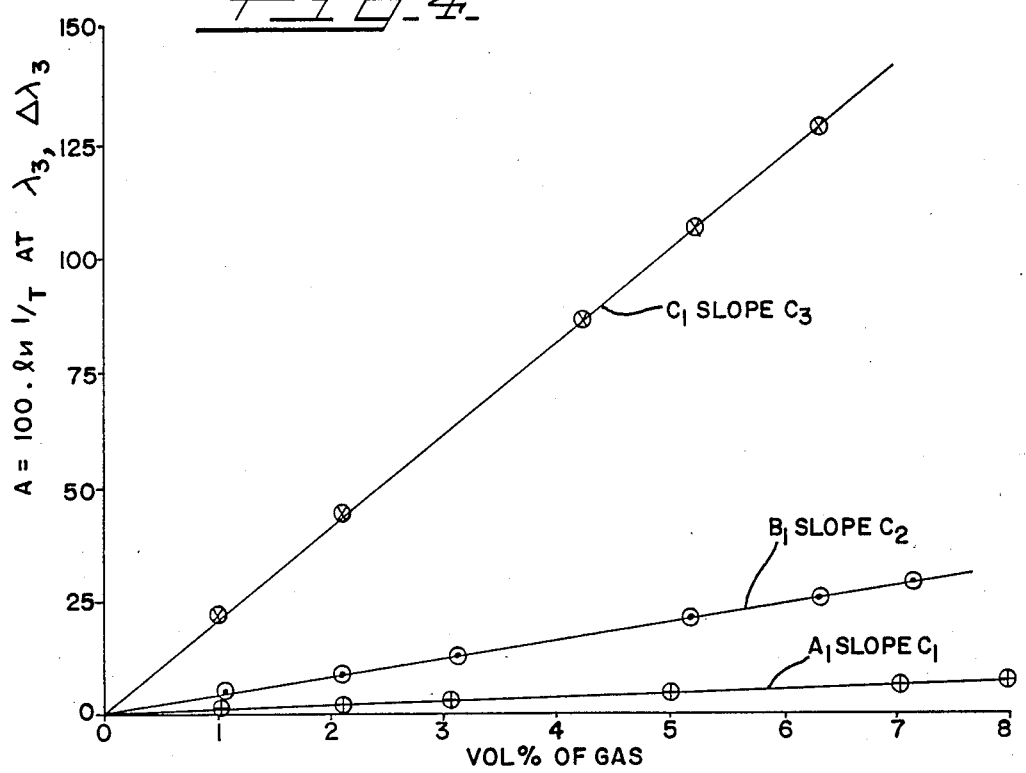
FIG-4-

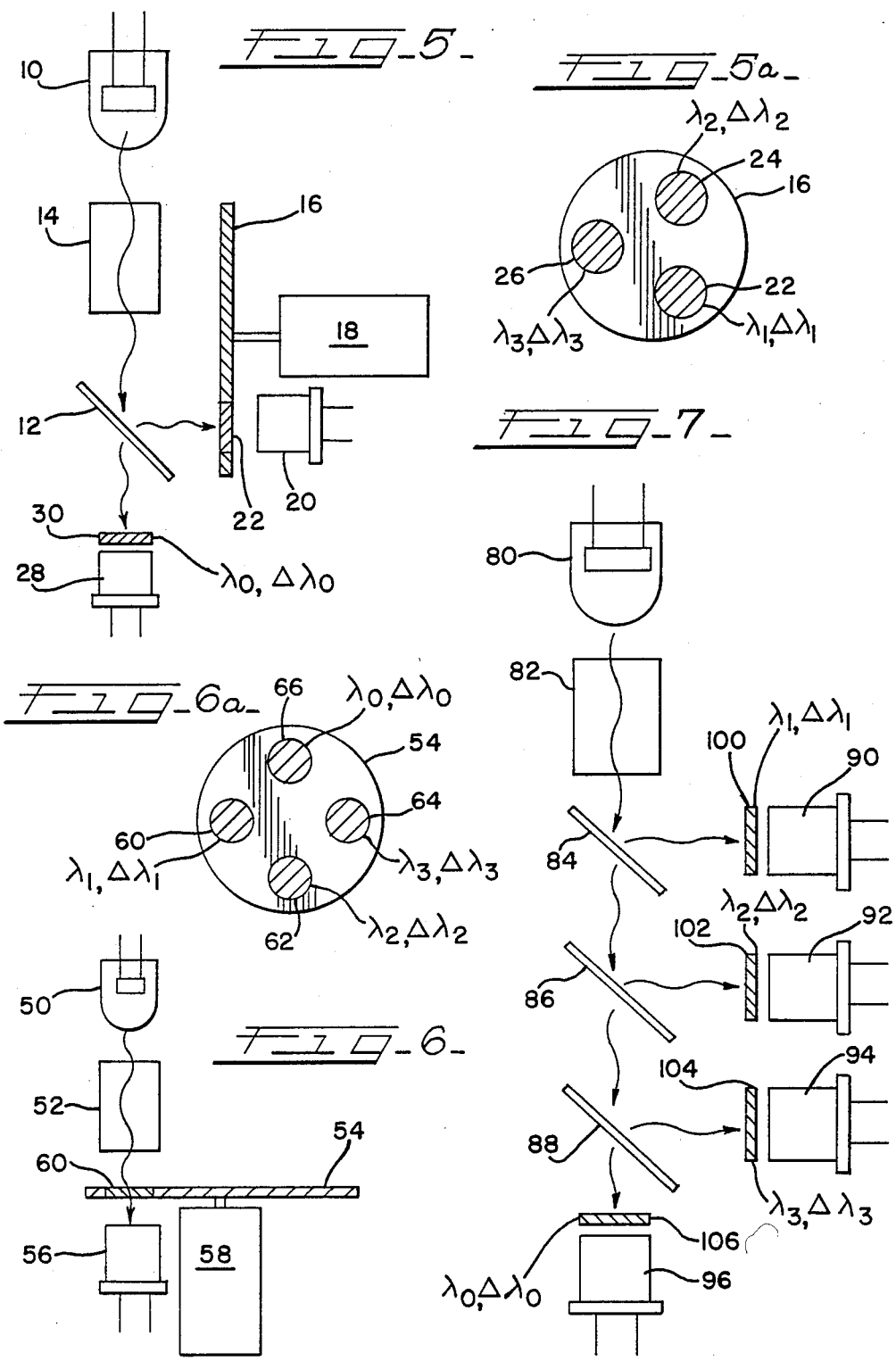

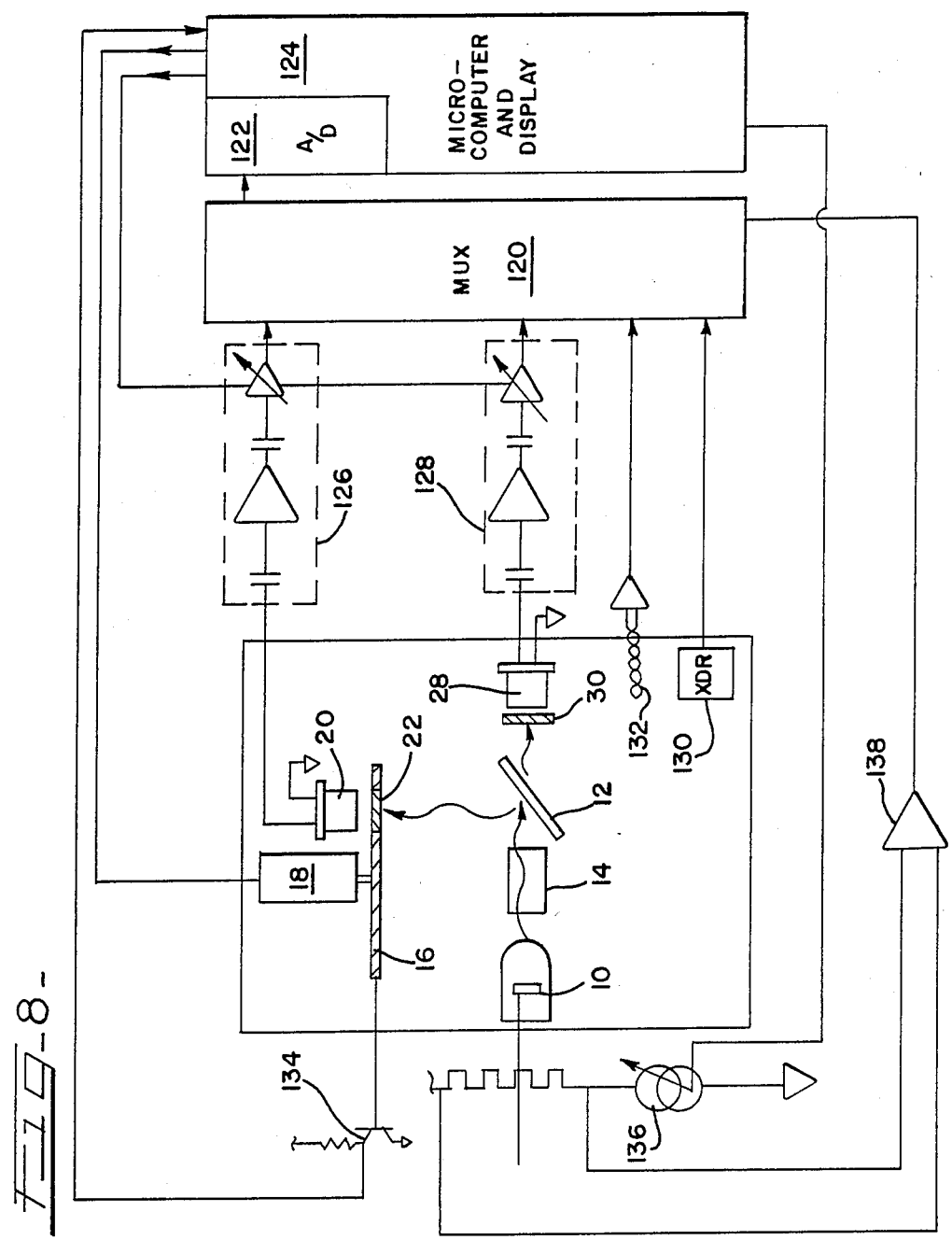

MULTIPLE COMPONENT GAS ANALYZER

BACKGROUND OF THE INVENTION

1. Field of the Invention

The present invention is in the field of nondispersive infrared (NDIR) gas analysis of a type tyically used to measure the concentration of specified gases in medical breath analyzers and in medical instruments. More particularly, the present invention relates to an improved NDIR gas analyzer which accurately measures the concentration of a selected one of a plurality of gases in a multi-component gas mixture.

2. The Prior Art

The term "nondispersive" as used herein refers to the apparatus used, typically a narrow-band optical or infrared filter instead of a prism or diffraction grating, for isolating radiation in a particular wavelength band for measurement purposes. The isolated wavelength band normally coincides with a strong absorption band in the absorption spectrum of a gas to be measured.

The NDIR technique has been widely used in the gas analyzer industry for the detection of single-component and multi-component gas mixtures. Such gas analyzers utilize the principle that various gases exhibit substantial absorption charactristics at specific wavelengths in the infrared radition spectrum. Several types of these gas analyzers exist which utilize a number of arrangements of components such as the source, sample chamber, optical filter, reference cell and detector. In one such gas analyzer shown and described in U.S. Pat. No. 3,793,525 by Burch et al. the beam of infrared energy passing through the sample chamber containing the unknown gas mixture is varied by the interposition of one or more narrow band-pass filters such as on a filter wheel in the path of the infrared energy beam. Typically, each filter only passes radiation at the characteristic absorption wavelength of a particular gas of interest. Another filter may also be used as a reference filter at a wavelength close to but not overlapping the characteristic absorption wavelength of any of the gases present in the sample cell. This type of gas analyzer also requires the generation of some type of synchronizing signal in order to coordinate the operation of the signal processing circuitry with the rotation of the filter wheel.

Another type of NDIR gas analyzer is shown and described in U.S. Pat. No. 3,811,776 by Blau Jr. which incorporates in addition to the infrared source, sample chamber, narrow band-pass filter and detector, a reference cell (a gas cell containing the gas of interest, in this case $CO_2$) and an identical cell evacuated or filled with a gas that is transparent at the wavelength used (4.26 microns for $CO_2$). These two cells alternately are moved into and out of the radiation beam. Since a sample chamber is placed in series with these cells, the alternate introduction of the absorbing and nonabsorbing cells into the radiation beam creates a reference (absorbing or reference cell) and a sample (non-absorbing cell) detector signal whose ratio is used to determine the $CO_2$ gas concentration in the sample chamber. Unlike the configuration described in U.S. Pat. No. 3,793,525 alluded to earlier which utilizes two interposed optical filters to create a sample and reference detector signal, the Blau configuration takes advantage of the principle of non-linear absorption by the gas to be measured ($CO_2$) as discussed in U.S. Pat. No. 4,578,762 by Wong in order to create the reference and sample signals.

Yet another and improved type of such gas analyzer is shown and described in U.S. Pat. No. 4,694,173 by Wong. This gas analyzer has no moving parts such as a rotating wheel for effecting either the interposition of optical filters or absorbing and non-absorbing cells to create both a sample and a reference detector signal as in the NDIR gas analyzers described earlier.

All of the NDIR gas analyzers described hitherto for the measurement of the concentrations of one or more gases in a mixture assume the fundamental fact that the infrared absorption bands of these gases are respectively specific, i.e. they do not spectrally overlap in the radiation spectrum. As a matter of fact none of the above types of NDIR gas analyzers will function as intended if the gas or gases to be measured have nonspecific absorption bands in the infrared portion of the electromagnetic spectrum. Under this circumstance they will all suffer significant interferences from other gases that share a portion of their absorption bands and will be rendered unacceptably inaccurate in many or even almost all applications.

The NDIR technique has been widely accepted over the years in the gas analyzer industry primarily because the gases of interest for both medical and industrial applications typically have strong and specific absorption bands in the infrared. On the medical side the very strong and specific 4.26 micron absorption band of $CO_2$ is directly attributable to the success and acceptance of the NDIR $CO_2$ gas analyzer. On the industrial side such as in the area of automotive exhaust emission monitoring, the principal gases (hydrocarbons, CO and $CO_2$) all have strong and specific absorption bands at 3.3-3.4, 4.67 and 4.26 microns, respectively.

There are instances where the gases that need to be measured simultaneously have very significantly overlapping absorption bands in the infrared. A well-known example is the case of the anesthetic halocarbons Halothane, Enflurane and Isoflurane. These three gases, being hydrocarbon derivatives, have relatively weak absorption bands bunched together in the 3.3-3.5 micron region, much like the other hydrocarbons. However, they also have strong but overlapping absorption bands beyond the 3.3-3.4 micron region extending all the way to 16 microns. Since these gases are very important to the field of medicine espcially in the practice of anaesthesia, instruments are needed for their accurate and precise measurement.

Monitors based upon several different physical principles have been available for use in measuring anesthetic halocarbons, e.g. elastomer string, coated piezoelectric crystal, refractometer, gas chromatograph, spectrophotometers operating in the ultraviolet and infrared ranges, and mass spectrometer. Except for infrared and mass spectrometers, these methods have been less than satisfactory for routine clinical use, because of deficiencies such as bulky sensors, interference by carbon dioxide, nitrous oxide and water vapor, and excessive drift of zero and gain.

Although the mass spectrometer has dominated the field of anesthetic halocarbon measurement over the years, NDIR analyzers for these gases do exist side by side with the mass spectrometer. These NDIR anesthetic halocarbon analyzers utilize both the strong 8-14 micron and the much weaker 3.3-2.5 micron absorption bands for their measurement. However, due to the overlapping characteristics of their absorption bands at these wavelengths, all halocarbons (Halothane, Enflurane, and Isoflurane) are measured at the same wavelength band defined by one appropriately chosen band-pass filter. Different gain factors are used in the signal processing circuitry to set proper sensitivity for each halocarbon as disclosed and described in U.S. Pat. No. 4,480,190 by Burough et. al. With this approach specific halocarbons cannot be automatically identified and the user must manually designate the halocarbon being measured. Furthermore these NDIR instruments show much poorer performance in terms of sensitivity, specificity and stability when compared to their counterparts for the measurement of other gases such as $CO_2$, CO and methane. For those instruments which use the weak 3.3–3.4 micron absorption band the modulation is hardly sufficient to allow a good measurement. This leads to poor sensitivity, a bulky sample chamber and vulnerability to interference from other gases, albeit at moderate levels. Thus a need exists for an improved approach for the detection and analysis of these gases.

As expectations for the practice of safe medicine continue to grow (partly because of the increase in the number of operating room malpractice suits being filed and partly because of the general awareness of the possible disasters that an average patient may face) the need for an improved anesthetic halocarbon monitor becomes more urgent. In addition to better sensitivity, specificity and stability that are expected of these instruments, the ability to automatically identify individual halocarbons is crucial. At the least these instruments should possess the capability to inform the anesthesiologist that a different halocarbon is being administered to the patient other the one he thinks is being delivered. No presently available halocarbon monitor known to the inventors possesses this desirable feature.

SUMMARY OF THE INVENTION

An important object of this invention is to provide a monitor that is able to identify automatically specific halocarbons, thus eliminating the potentially fatal hazards of delivering the wrong anesthetic gas to the patient.

It is another object of the present invention to provide an improved NDIR gas analyzer that reliably measures the concentration of gases having significantly overlapping absorption bands in the infrared.

It is further object of this invention to provide such an analyzer that automatically identifies the concentration of specific gases in a multi-component gas mixture.

According to this invention, a gas analyzer is provided for N gases having overlapping absorption spectra, where N is an integer greater than 1. This analyzer includes a source operative to generate at least one measuring beam, a sample cell adapted to contain a gas to be analyzed, and means for passing at least one measuring beam through the sample cell. First means are provided responsive to at least one measuring beam for generating N measuring signals, each indicative of optical energy from the source transmitted through the sample cell in a respective optical region characterized by a respective optical center wave-length $\lambda_i$ and a respective band pass, $\Delta\lambda_i$ where i is an integer greater than 0 and less than or equal than N. Second means are provided, responsive to the N measuring signals, for combining the N measuring signals to automatically determine which of the N gases is present in the sample cell in the greatest concentration, and the concentration thereof.

As described below, in the preferred embodiments the optical center wave-lengths and band passes are selected such that each of the N measuring signals is a linear function of concentration of each of the N gases. When this is the case, linear algebra can be used to determine the concentrations of the N gases. As pointed out below, this invention is not limited to any particular optical or signal processing layout, and it can be used in systems with either AC modulated or DC sources and either in systems utilizing rotating filter wheels, or in systems with no moving filters or choppers.

The invention itself, together with further objects and attendant advantages, will best be understood by reference to the following detailed description, taken in conjunction with the accompanying drawings.

BRIEF DESCRIPTION OF THE DRAWINGS

FIG. 1 shows the spectral transmittance curves of three gases A, B and C having overlapping absorption bands.

FIG. 2 shows the spectral absorbance versus concentration curves for gases A, B and C using bandpass filter $\lambda_1$ with FWHM=$\Delta\lambda_1$;

FIG. 3 shows the spectral absorbance versus concentration curves for gases A, B and C using bandpass filter $\lambda_2$ with FWHM=$\Delta\lambda_2$;

FIG. 4 shows the spectral absorbance versus concentration curves for gases A, B and C using bandpass filter $\lambda_3$ with FWHM=$\Delta\lambda_3$;

FIG. 5 is a schematic diagram showing the optical system of a first preferred embodiment of the multicomponent gas analyzer of the present invention;

FIG. 5a is a plan view of the filter wheel of FIG. 5.

FIG. 6 is a schematic diagram showing the optical system of a second preferred embodiment of the multicomponent gas analyzer of the present invention;

FIG. 6a is a plan view of the filter wheel of FIG. 6.

FIG. 7 is a schematic diagram showing the optical system of a third alternate preferred embodiment of the multicomponent gas analyzer of the present invention;

FIG. 8 is an electronic block diagram of the signal processing circuitry for the first preferred embodiment of FIG. 5.

DETAILED DESCRIPTION OF THE PRESENTLY PREFERRED EMBODIMENTS

As mentioned above, the standard NDIR techniques for gas analysis break down when the gases to be measured have non-specific or overlapping absorption bands in the infrared. FIG. 1 shows schematically as an example the spectral transmittance curves for three gases A, B and C having overlapping absorption bands. Note that a standard NDIR technique using a bandpass filter centered at $\lambda_1$ and having a full width at half maximum (FWHM) equal to $\Delta\lambda_1$ as illustrated in FIG. 1 as the shaded area will not discriminate between the three gases as all three gases A, B and C have varying absorption coefficients within this spectral band. The same situation is true for N gases where N>1. For the case when the FWHM or $\Delta\lambda_1$ is relatively small (e.g. a few tenths of a micron), the mean spectral transmittance over the spectral interval $\Delta\lambda_1$ can be expressed approximately using the averaged absorption coefficients for gases A, B and C as follows:

$$\left.\frac{T}{T_o}\right|_{\lambda_1,\Delta\lambda_1} = e^{-\bar{k}_A c_A l} \cdot e^{-\bar{k}_B c_B l} \cdot e^{-\bar{k}_C c_C l} + \bar{D}_{\lambda_1} \quad (1)$$

where $\bar{k}_A$, $\bar{k}_B$ and $\bar{k}_C$ are the averaged absorption coefficients for gases A, B and C respectively over the spectral interval $\Delta\lambda_1$; $c_A$, $c_B$ and $c_C$ are the concentrations of the respective gases, and $l$ is the pathlength of the gas sample containing gases A, B and C. The quantity $\bar{D}_{\lambda_1}$ is called the residual spectral transmittance, meaning that even if the absorption term $e^{-\bar{k}_A c_A l} \cdot e^{-\bar{k}_B c_B l} \cdot e^{-\bar{k}_C c_C l}$ goes to zero the spectral transmittance $T/T_o$ does not vanish, but equals. Note that in expressing the spectral transmittance as the product of three exponentials one implies that the absorption of radiation by the gases obeys Beer's Law exactly. In general this is not true for real gases but is a good approximation under certain conditions as set out in the paragraphs below AS expressed in Equation (1) above $\bar{k}_A$, $\bar{k}_B$ and $\bar{k}_C$ and $l$ and are known and $c_A$, $c_B$ and $c_C$ are the unknowns for the gas sample to be measured. Since only one spectral transmittance measurement is made in the standard NDIR technique it is impossible to determine which gases or combination of gases lead to the measured spectral transmittance value. Mathematically speaking, one has one equation with three unknowns and the solutions for $c_A$, $c_B$ and $c_C$ are therefore intractable if only one measurement is made for $T/T_o$.

By expanding Equation (1) into a set of three equations involving three narrow bandpass filters centered at $\lambda_1$, $\lambda_2$ and $\lambda_3$, namely, $$\left.\frac{T}{T_o}\right|_{\lambda,\Delta\lambda_1} = e^{-k_{A1}C_A l} \cdot e^{-k_{B1}C_B l} \cdot e^{-k_{c1}C_c l} + D_{\lambda_1} \quad (2)$$

$$\left.\frac{T}{T_o}\right|_{\lambda_2,\Delta\lambda_2} = e^{-k_{A2}C_A l} \cdot e^{-k_{B2}C_B l} \cdot e^{-k_{c2}C_c l} + D_{\lambda_2} \quad (3)$$

$$\left.\frac{T}{T_o}\right|_{\lambda_3,\Delta\lambda_3} = e^{-k_{A3}C_A l} \cdot e^{-k_{B3}C_B l} \cdot e^{-k_{c3}C_c l} + D_{\lambda_3} \quad (4)$$

one has a theoretically tractable situation. Since $\bar{k}_{A1}$, $\bar{k}_{A2}$, $\bar{k}_{A3}$ ... $\bar{k}_{C2}$, $\bar{k}_{C3}$, $l$ and $\bar{D}_{\lambda_1}$, $\bar{D}_{\lambda_2}$ and $\bar{D}_{\lambda_3}$ are are all known or can be determined by a set of appropriate initial conditions, one is left with three equations and three unknowns and the situation is theoretically solvable. However upon closer scrutiny the situation is actually quite complicated as the three equations are all non-linear and therefore not readily solvable. Without the availability of a high speed main-frame computer it will generally require a long time to solve these equations. It is therefore apparent that the standard NDIR technique, expanded or otherwise, is not conventionally well suited to measure gases having significantly overlapping absorption bands.

In order for the basic NDIR technique to work for gases having overlapping absorption bands the present inventors developed a novel spectral correlation technique that uses a set of filters whose center wavelengths and FWHM's render the gas analysis problem amenable to mathematically simple solutions. This novel spectral correlation technique is applicable to any number of gases. As will be described in detail below for the case of three gases, the spectral correlation technique of this invention simplifies the three non-linear equations (Equations 2–4 above) into three substantially linear ones enabling their solution with the use of standard matrix algebra within acceptable accuracies.

The present inventors recognized the fact that if Equations 2–4 shown above could be used to represent the absorption of radiation by the gases A, B and C (i.e. Beer's Law is rigidly obeyed), and if the residual spectral transmittance terms $\bar{D}_{\lambda_1}$, $\bar{D}_{\lambda_2}$ and $\bar{D}_{\lambda_3}$ could be made to vanish, then these equations could be rewritten as three linear equations as follows:

$$\alpha = \ln T_o/T|_{\lambda_1} = a_1 c_A + b_1 c_B + c_1 c_C \quad (5)$$

$$\beta = \ln T_o/T|_{\lambda_2} = a_2 c_A = b_2 c_B = c_2 c_C \quad (6)$$

$$\alpha = \ln T_o/T|_{\lambda_3} = a_3 c_A + b_3 c_B + c_3 c_C \quad (7)$$

where
$a_1 = \bar{k}_{A1}, l$
$b_1 = \bar{k}_{B1}, l$
$c_1 = \bar{k}_{C1}, l$
$b_3 = \bar{k}_{B3}, l$
$c_3 = \bar{k}_{C3}, l$ etc.

Under this condition the coefficients $a_1, b_1, c_1, \ldots c_3$ can be determined by the choice of appropriate initial conditions. For example by choosing $c_B = c_C = 0$, one has $$a_1 = (1/c_A)\ln T_o/T|_{\lambda_1} \quad (8)$$

$$a_2 = (1/c_A)\ln T_o/T|_{\lambda_2} \quad (9)$$

$$a_3 = (1/c_A)\ln T_o/T|_{\lambda_3} \quad (10)$$

Thus by first normalizing the spectral transmittance, namely setting $T = T_o$ when there is no gas in the sample chamber or $c_A = c_B = 0$, one can obtain the values of $a_1$, $a_2$ and $a_3$ through the measured values of $\ln T_o/T|_{\lambda_1}$, $\ln T_o/T|_{\lambda_2}$ and $\ln T_o/T|_{\lambda_3}$ for a known value of $c_A$ using Equations 8–10.

Similarly the coefficients $b_1, b_2, b_3 \ldots c_2, c_3$ can be determined using appropriate initial conditions as illustrated for $a_1, a_2, a_3$ above. Equations 5–7 can be rewritten in matrix form as:

$$\begin{pmatrix} \alpha \\ \beta \\ \alpha \end{pmatrix} = \begin{pmatrix} a_1 & b_1 & c_1 \\ a_2 & b_2 & c_2 \\ a_3 & b_3 & c_3 \end{pmatrix} \begin{pmatrix} C_A \\ C_B \\ C_C \end{pmatrix} = M \begin{pmatrix} C_A \\ C_B \\ C_C \end{pmatrix} \quad (11)$$

or one can express $c_A$, $c_B$, $= c_C$ in terms of $\alpha$, $\beta$ and $\gamma$ as follows:

$$\begin{pmatrix} C_A \\ C_B \\ C_C \end{pmatrix} = M^{-1} \begin{pmatrix} \alpha \\ \beta \\ \alpha \end{pmatrix} \quad (12)$$

where $M^{-1}$ is the inverse of the matrix M. Since M is known (i.e. all the elements $a_1, b_1, c_1 \ldots$ etc. are known), $M^{-1}$ can be readily determined using standard matrix algebra. Thus $c_A$, $c_B$, $c_C$ can be determined using Equation 12 if $\alpha$, $\beta$ and $\gamma$ are measured.

According to the present invention, a series of analytical steps we defined aimed at establishing a measurement condition such that the absorption of radiation by the gases can be adequately approximated within the acceptable accuracy limit by Beer's Law through Equations 2–4 above for the case of three gases A, B and C.

Furthermore, the establishment of such measurement conditions minimizes the values of the residual spectral transmittances $\overline{D}_{\lambda 1}$, $\overline{D}_{\lambda 2}$ and $\overline{D}_{\lambda 3}$ in Equations 2-4 to the extent that these equations can be solved through the use of simple matrix algebra as illustrated in the above paragraphs.

A novel approach is used to correlate the measured normalized spectral transmittance curves for the relevant gases to the normalized wavelength-dependent absorption coefficients, namely $k(\lambda)$. The relation used in this technique is given by:

$$T(\lambda) = T(Min.)^{k(\lambda)}$$

where $T(\lambda)$ is the normalized spectral transmittance and $T(Min.)$ is the minimum of $T(\lambda)$ over the spectral region of interest. Thus all the absorption coefficients for the gases can be correlated to the absorption coefficients at $\lambda$min at which $T(\lambda) = T_{min}$ for the respective gases.

The following series of analytical steps can be used to select appropriate bandpasses filter characteristics. 1. The spectral transmittance is represented in the form of normalized absorbance, namely $\ln 1/T$, where $T$ is the transmittance ($T_o = 1$ for 100% transmittance). The adoption of this representation greatly simplifies the computer simulation that is required for the optimum selection of the bandpass filter characteristics, namely the center wavelength and the FWHM for each filter. 2. For the case of three gases having overlapping absorption spectra such as those shown in FIG. 1 the center wavelength for each of the three bandpass filters is selected to ensure that each of the three bandpass filters singles out a dominant absorption of only one of the three gases but not the other two. 3. Once the center wavelengths for the three bandpass filters are selected their respective FWHM's are determined via computer simulation such that the absorption of radiation by the gases adheres to Beer's Law according to a preset set of criteria. Furthermore, such a selection of FWHM's for the filters also ensures the suppression of the residual spectral transmittances, $\overline{D}_{\lambda 1}$, $\overline{D}_{\lambda 2}$ and $\overline{D}_{\lambda 3}$ to an acceptable minimum. 4. In order to carry out steps 2 and 3 a computer simulation program is set up to perform the needed iterative steps in order to find and verify the optimum parameters for the bandpass filters that will yield the desired results. For a given selected $\lambda_i$ and FWHM = $\Delta\lambda_i$ the computer simulation program calculates $\ln 1/T$ or the normalized absorbance as a function of the concentration of gas i. Sufficient data points are generated to perform a least square fit variance test to see whether the equation $\ln 1/T$ vs c (concentration) is indeed a straight line within the specified accuracy. When the normalized absorbance approach, namely $\ln 1T$ vs c (concentration), is used the residual spectral transmittance term $\overline{D}_{\lambda i}$ manifests itself as a variance of the straight line fit to the $\ln 1/T$ vs c curve. This is because $\ln 1/T$ always passes through the origin when the concentration of a gas is zero and $T = 1$. Thus if the $\ln 1/T$ vs c curve is a straight line as determined by the least square variance fit parameter then not only the absorption of the radiation by the gases within the respective bandpass filters obeys Beer's Law, but also the residual spectral transmittance terms are all reduced to zero or an acceptable minimum.

FIGS. 2-4 show graphically the results of steps 1-4 as applied to a mixture of three gases A, B and C. Spectral bandpass filters ($\lambda 1$, $\Delta\lambda 1$), ($\lambda 2$, $\Delta\lambda 2$) and ($\lambda 3$, $\Delta\lambda 3$) are used respectively for FIGS. 2, 3 and 4. Note that should the choice for the filter parameters be non-optimum then the $\ln 1/T$ vs c curve for that particular gas will deviate from a straight line as indicated by the dashed curves in FIG. 2. $\lambda_i$ and $\Delta\lambda_i$ are adjusted to ensure that $\ln 1/T$ is a linear function of concentration (within the given accuracy).

Based upon the results of FIGS. 2, 3 and 4 one can readily write:

$$\lambda_1: \ln 1/T_1 = a_1 c_A + a_2 c_B + a_3 c_C \quad (13)$$

$$\lambda_2: \ln 1/T_2 = b_1 c_A + b_2 c_B + b_3 c_C \quad (14)$$

$$\lambda_3: \ln 1/T_3 = c_1 c_A + c_2 c_B + c_3 c_C \quad (15)$$

where ($a_1$, $a_2$, $a_3$), ($b_1$, $b_2$, $b_3$), and ($c_1$, $c_2$, $c_3$) are the slopes of the straight lines for gases A, B and C in FIGS. 2, 3 and 4 respectively.

Equations 13-15 can be written in matrix notation as:

$$\begin{pmatrix} \ln 1/T_1 \\ \ln 1/T_2 \\ \ln 1/T_3 \end{pmatrix} = \begin{pmatrix} a_1 & a_2 & a_3 \\ b_1 & b_2 & b_3 \\ c_1 & c_2 & c_3 \end{pmatrix} \begin{pmatrix} c_A \\ c_B \\ c_C \end{pmatrix} \quad (16)$$

and the solutions for the respective concentrations for the gases present in the mixture, namely $c_A$, $c_B$ and $c_C$ are:

$$\begin{pmatrix} c_A \\ c_B \\ c_C \end{pmatrix} = \begin{pmatrix} a_1 a_2 a_3 \\ b_1 b_2 b_3 \\ c_1 c_2 c_3 \end{pmatrix}^{-1} \begin{pmatrix} \ln 1/T_1 \\ \ln 1/T_2 \\ \ln 1/T_3 \end{pmatrix} \quad (17)$$

As alluded to earlier, the values for the slopes $a_1$, $a_2$, ... $c_3$ etc. can be determined experimentally during initial calibration for the instrument. These values are stored in memory and used subsequently in the computation for the concentrations of the gases in question. Thus with the use of Equation 17 above the respective concentrations of three gases having overlapping absorption bands can be determined by the measurement of spectral transmittance values with the three respective bandpass filters.

The techniques described above can be implemented in a wide variety of optical and signal processing systems. FIGS. 5, 6 and 7 show three suitable optical systems that can be used to implement this invention.

The optical system of FIG. 5 includes an AC infrared source 10 which produces a beam of infrared radiation that passes through a sample chamber chamber 14 to a beam splitter 12. The beam splitter 12 directs a portion of the incident radiation to a filter wheel 16, and radiation that passes through the filter wheel 16 is detected by a detector 20. A stepper motor 18 rotates the filter wheel 16 to place any one of three filters 22, 24, 26 between the detector 20 and the beam splitter (FIG. 5a). Radiation which passes through the beam splitter 12 first passes through a filter 30 and then strikes a detector 28. By way of example, the three filters 22, 24, 26 on the filter wheel 16 can be filters for the wave-lengths $\lambda_1$, $\lambda_2$, $\lambda_3$, discussed above, and the filter 30 can be chosen for the reference beam at $\lambda_o$. It should be apparent that the optical system of FIG. 5 generates four measuring signals which can be used as described above to detect the concentration of three separate gases.

FIG. 6 shows a second preferred optical system suitable for use with this invention. This system includes an DC infrared source 50 which generates an optical beam that passes through a sample chamber 52 and then strikes a filter wheel 54. Radiation passing through the filter wheel 54 strikes an infrared detector 56 which generates measuring signals. The rotational position of the filter wheel 54 is determined by a motor 58 such as a stepper motor. As shown in FIG. 6a, the filter wheel 54 includes four filters 60, 62, 64, 66 for wave-lengths $\lambda_1, \lambda_2, \lambda_3, \lambda_o$, as discussed above.

FIG. 7 shows a third preferred optical system for implementing this invention. This third system includes an AC infrared source 80 which generates an optical beam which passes through a sample chamber 82 and is then directed through a sequence of three beam splitters 84, 86, 88. The portion of the infrared beam deflected by each of the beam splitters is directed to a respective detector 90, 92, 94, via a respective interference filter 100, 102, 104. Infrared radiation that passes through all of the beam splitters 84, 86, 88 strikes a fourth detector 96 via a fourth filter 106. The four filters 100, 102, 104, 106 can be selected for the wave-lengths $\lambda_1, \lambda_2, \lambda_3, \lambda_o$, as described above.

FIG. 8 shows a block diagram of a gas analyzer that incorporates the optical system of FIG. 5. This gas analyzer includes a multiplexer 120, an analog to digital converter 122, and a microcomputer and display 124. The two detectors 20, 28 provide measuring signal inputs to the multiplexer 120 via signal processing circuitry 126, 128. Additionally, the multiplexer 120 receives analog inputs from a pressure transducer 130 and a thermistor 132. The microcomputer also receives inputs from a filter wheel position sensor 134 and a IR source power sensor 138. The microcomputer 124 controls a current source 136 and adjustable gains on the two signal processing circuits 126, 128.

Simply by way of example, the following parameters have been found suitable for use in the embodiment of FIGS. 5 and 8. Of course, these details of construction are in no way intended to be limiting.

With respect to the filters 22, 24, 26, 30, the following parameters have been found suitable.

| Filter No. | $\lambda_i$ | $\Delta\lambda_i$ |
|---|---|---|
| 22-$\lambda_1$ | 12.3 micron | 0.21 micron |
| 24-$\lambda_2$ | 8.24 micron | 0.15 micron |
| 26-$\lambda_3$ | 8.70 micron | 0.50 micron |
| 30-$\lambda_0$ | 10.6 micron | 0.26 micron |

These filters were selected for detection of Halothane Enflurane and Isoflurane, and with these filters the matrices M and $M^{-1}$ discussed above can be calculated. The matrix $M^{-1}$ can be used to calculate the concentrations for the three gases Halothane, Enflurane, Isoflurane ($C_H, C_E, C_F$) according to the following equations:

$$C_H = -.0193A_1 + .00437A_2 + .206A_3 \quad (18)$$

$$C_E = .0589A_1 - .0531A_2 - .0253A_3 \quad (19)$$

$$C_F = -.0155A_1 + .0632A_2 - .0277A_3 \quad (20)$$

In these equations $A_1, A_2,$ and $A_3$ are equal to the normalized absorbance $\ln T_o/T_x|_{\lambda_i}$ of the signals passing through filters $\lambda_1, \lambda_2, \lambda_3$, respectively, as defined in equations 5 through 7 above.

The basic steps performed by the microcomputer 124 are first to measure the detector signals associated with the four filters 22, 24, 26, 30 and then to determine the corresponding four transmittances $T_1, T_2, T_3, T_O$. Equations 5 through 7 are then used to determine $A_1, A_2,$ and $A_3$ which correspond to $\alpha, \beta,$ and $\gamma$ of Equations 5 through 7. $A_1, A_2,$ and $A_3$ are then used in the foregoing Equations 18-20 to determine the concentrations of Halothane, Enflurane and Isoflurane, respectively. The microcomputer 124 then displays the concentrations of Halothane, Enflurane, and Isoflurane on the display 124. Alternately, in most medical settings only one of the three gases will be present in any concentration, and the display can instead indicate the identity of the single gas present and its concentration.

Of course, it should be understand that a wide range of changes and modifications can be made to the preferred embodiments described above. It is therefore intended that the foregoing detailed description be regarded as illustrative rather than limiting, and that it be understood that it is the following claims, including all equivalents, which are intended to define the scope of this invention.

I claim:

1. In a gas analyzer for N gases having overlapping absorption spectra, where N is an integer greater than 1, said analyzer of the type comprising a sample cell adapted to contain a gas to be analyzed and a source operative to generate at least one measuring beam which passes through the sample cell, the improvement comprising:

means, responsive to the at least one measuring beam, for generating N measuring signals, each indicative of optical energy from the source transmitted through the sample cell in a respective optical region characterized by a respective optical center wavelength $\lambda_i$ and a respective bandpass $\Delta\lambda_i$, where i is an integer greater than 0 and less than or equal to N;

means, responsive to the N measuring signals, for combining the N measuring signals to automatically determine which of the N gases is present in the sample cell in the greatest concentration and the concentration thereof.

2. The invention of claim 1 wherein the automatically determining means comprises:

means for automatically determining the concentrations of each of the N gases in the sample cell.

3. The invention of claim 2 further comprising:

means for displaying the determined concentrations of each of the N gases in the sample cell.

4. The invention of claim 1 further comprising:

means for displaying the identity of the gas determined by the second means and the concentration thereof.

5. The invention of claim 1 wherein each of the N measuring signals is indicative of normalized absorbance in the respective optical region.

6. The invention of claim 1 wherein $\lambda_i$ and $\Delta\lambda_i$ are selected such that each of the N measuring signals is a substantially linear function of concentration of each of the N gases in the sample cell.

7. The invention of claim 6 wherein each of the N gases is characterized by significant absorption in each of the N optical regions.

8. The invention of claim 6 wherein the second means comprises means for algebraically combining the N measuring signals to determine the concentration of each of the N gases in the sample cell.

9. The invention of claim 8 wherein N equals 3, and $\lambda_i$ and $\Delta\lambda_i$ have the following values:
$\lambda_1 = 12.3$ micron
$\lambda_2 = 8.24$ micron
$\lambda_3 = 8.70$ micron
$\Delta\lambda_1 = 0.21$ micron
$\Delta\lambda_2 = 0.15$ micron
$\Delta\lambda_3 = 0.50$ micron.

10. In a gas analyzer for N gases having overlapping absorption spectra, where N is an integer greate than 1, said analyzer of the type comprising a sample cell adapted to contain a gas to be analyzed, and a source operative to generate at least one measuring beam passing through the sample cell, the improvement comprising:
N optical filters, each having a center wavelength $\lambda_i$ and an optical band pass $\Delta\lambda_i$, where i is an integer greater than 0 and less than or equal to N;
means for generating N measuring signals, each in response to a portion of the measuring beam filtered by the respective filter, $\lambda_i$ and $\Delta\lambda_i$ chosen for each filter such that the respective measuring signal is a substantially linear function of concentration of each of the N gases in the sample cell, and;
means for algebraically combining the N measuring signals to automatically determine the concentrations of each of the N gases in the sample cell.

11. The invention of claim 10 further comprising:
means for displaying the determined concentrations of each of the N gases in the sample cell.

12. The invention of claim 10 wherein each of the N measuring signals is indicative of normalized absorbance in the respective optical region.

13. The invention of claim 10 wherein each of the N gases is characterized by significant absorption in each of the N optical regions.

14. The invention of claim 10 wherein N equals 3, and $\lambda_i$ and $\Delta\lambda_i$ have the following values:
$\lambda_1 = 12.3$ micron
$\lambda_2 = 8.24$ micron
$\lambda_3 = 8.70$ micron
$\Delta\lambda_1 = 0.21$ micron
$\Delta\lambda_2 = 0.15$ micron
$\Delta\lambda_3 = 0.50$ micron.

* * * * *

UNITED STATES PATENT AND TRADEMARK OFFICE
CERTIFICATE OF CORRECTION

PATENT NO. : 4,914,719
DATED : April 3, 1990
INVENTOR(S) : Brendan Conlon et al.

Page 1 of 10

It is certified that error appears in the above-identified patent and that said Letters Patent is hereby corrected as shown below:

On the cover page under the heading "Inventors", after "Wis." please insert --Edward Zuperku, Elm Grove, Wis.--.

In column 1, line 26, please delete "charactristics" and substitute therefor --characteristics--.

In column 1, line 27, please delete "radition" and substitute therefor --radiation--.

In column 2, line 42, please delete "3.5" and substitute therefor --3.4--.

In column 2, line 47, please delete "espcially" and substitute therefor --especially--.

In column 2, line 66, please delete "2.5" and substitute therefor --3.4--.

UNITED STATES PATENT AND TRADEMARK OFFICE
CERTIFICATE OF CORRECTION

PATENT NO. : 4,914,719
DATED : April 3, 1990
INVENTOR(S) : Brendan Conlon et al.

It is certified that error appears in the above-identified patent and that said Letters Patent is hereby corrected as shown below:

IN THE DETAILED DESCRIPTION OF
THE PRESENTLY PREFERRED EMBODIMENTS

In column 5, line 1, please delete Equation No. 1 and substitute therefor $$-- \left.\frac{T}{T_c}\right|_{\lambda_i, \Delta\lambda_i} = e^{-\bar{k}_A C_A \ell} \cdot e^{-\bar{k}_B C_B \ell} \cdot e^{-\bar{k}_C C_C \ell} \cdot \bar{D}_{\lambda_i} \quad (1) --$$

In column 5, line 14, after "equals" please insert $$-- \bar{D}_{\lambda_1} --$$

In column 5, line 19, after "below" please insert --.--.

In column 5, line 19, please delete "AS" and substitute therefor --As--.

UNITED STATES PATENT AND TRADEMARK OFFICE
CERTIFICATE OF CORRECTION

PATENT NO. : 4,914,719
DATED : April 3, 1990
INVENTOR(S) : Brendan Conlon et al.

Page 3 of 10

It is certified that error appears in the above-identified patent and that said Letters Patent is hereby corrected as shown below:

In column 5, line 35, please delete Equation No. 2 and substitute therefor $$-- \left.\frac{T}{T_0}\right|_{\lambda_1, \Delta\lambda_1} = e^{-k_{A1} C_A \ell} \cdot e^{-k_{B1} C_B \ell} \cdot e^{-k_{C1} C_C \ell} + \frac{1}{D_{\lambda_1}} \quad (2) \quad --$$

In column 5, line 37, please delete equation No. 3 and substitute therefor $$-- \left.\frac{T}{T_0}\right|_{\lambda_2, \Delta\lambda_2} = e^{-k_{A2} C_A \ell} \cdot e^{-k_{B2} C_B \ell} \cdot e^{-k_{C2} C_C \ell} + \frac{1}{D_{\lambda_2}} \quad (3) \quad --$$

In column 5, line 41, please delete Equation No. 4 and substitute therefor $$-- \left.\frac{T}{T_0}\right|_{\lambda_3, \Delta\lambda_3} = e^{-k_{A3} C_A \ell} \cdot e^{-k_{B3} C_B \ell} \cdot e^{-k_{C3} C_C \ell} + \frac{1}{D_{\lambda_3}} \quad (4) \quad --$$

UNITED STATES PATENT AND TRADEMARK OFFICE
CERTIFICATE OF CORRECTION

PATENT NO. : 4,914,719
DATED : April 3, 1990
INVENTOR(S) : Brendan Conlon et al.

It is certified that error appears in the above-identified patent and that said Letters Patent is hereby corrected as shown below:

In column 5, line 45, please delete $\bar{D}\lambda 3$ and substitute therefor

-- $\bar{D}_{\lambda 3}$ --

In column 6, line 11, please delete Equation No. 5 and substitute therefor

-- $\alpha = \ln T_o/T \big|_{\lambda_1} = a_1 c_A + b_1 c_B + c_1 c_C \quad (5)$ --

In column 6, line 13, please delete Equation No. 6 and substitute therefor

-- $\beta = \ln T_o/T \big|_{\lambda_2} = a_2 c_A + b_2 c_B + c_2 c_C \quad (6)$ --

In column 6, line 15, please delete Equation No. 7 and substitute therefor

-- $\gamma = \ln T_o/T \big|_{\lambda_3} = a_3 c_A + b_3 c_B + c_3 c_C \quad (7)$ --

UNITED STATES PATENT AND TRADEMARK OFFICE
CERTIFICATE OF CORRECTION

PATENT NO. : 4,914,719
DATED : April 3, 1990
INVENTOR(S) : Brendan Conlon et al.

It is certified that error appears in the above-identified patent and that said Letters Patent is hereby corrected as shown below:

In column 6, line 18, please delete $$a_1 = \overline{k}_{A1}.1$$

and substitute therefor $$-- \ a_1 = \overline{k_{A1}} \cdot \ell \ --$$

In column 6, line 19, please delete $$b_1 = \overline{k}_{B1}.1$$

and substitute therefor $$-- \ b_1 = \overline{k_{B1}} \cdot \ell \ --$$

UNITED STATES PATENT AND TRADEMARK OFFICE
CERTIFICATE OF CORRECTION

PATENT NO. : 4,914,719
DATED : April 3, 1990
INVENTOR(S) : Brendan Conlon et al.

Page 6 of 10

It is certified that error appears in the above-identified patent and that said Letters Patent is hereby corrected as shown below:

In column 6, line 20, please delete $$c_1 = \overline{k}_{C1}.1$$

and substitute therefor $$-- \quad c_1 = \overline{k_{C1}} \cdot \ell \quad --$$

In column 6, line 21, please delete $$b_3 = \overline{k}_{B3}.1$$

and substitute therefor $$-- \quad b_3 = \overline{k_{B3}} \cdot \ell \quad --$$

UNITED STATES PATENT AND TRADEMARK OFFICE
CERTIFICATE OF CORRECTION

PATENT NO. : 4,914,719
DATED : April 3, 1990
INVENTOR(S) : Brendan Conlon et al.

It is certified that error appears in the above-identified patent and that said Letters Patent is hereby corrected as shown below:

In column 6, line 22, please delete $$c_3 = \overline{k}_{C3,1} \; etc.$$

and substitute therefor $$-- \; \dot{c}_3 = \overline{k_{C3}} \cdot \lambda \qquad etc. \; --$$

In column 6, line 27, please delete Equation No. 8 and substitute therefor $$-- \; a_1 = (1/c_A) \, \ln \, T_o/T \Big)_{\lambda_1} \qquad (8) \; --$$

In column 6, line 29, please delete Equation No. 9 and substitute therefor $$-- \; a_2 = (1/c_A) \, \ln \, T_o/T \Big)_{\lambda_2} \qquad (9) \; --$$

UNITED STATES PATENT AND TRADEMARK OFFICE
CERTIFICATE OF CORRECTION

PATENT NO. : 4,914,719
DATED : April 3, 1990
INVENTOR(S) : Brendan Conlon et al.

It is certified that error appears in the above-identified patent and that said Letters Patent is hereby corrected as shown below:

In column 6, line 31, please delete Equation No. 10 and substitute therefor $$a_3 = (1/c_A) \ln T_o/T \big|_{\eta_3} \quad , \quad (10)$$

In column 6, lines 44-48, please delete Equation No. 11 and substitute therefor $$\begin{pmatrix} \alpha \\ \beta \\ \gamma \end{pmatrix} = \begin{pmatrix} a_1 & b_1 & c_1 \\ a_2 & b_2 & c_2 \\ a_3 & b_3 & c_3 \end{pmatrix} \begin{pmatrix} c_A \\ c_B \\ c_C \end{pmatrix} = M \begin{pmatrix} c_A \\ c_B \\ c_C \end{pmatrix} \quad (11)$$

In column 6, lines 53-55, please delete Equation No. 12 and substitute therefor --

$$\begin{pmatrix} c_A \\ c_B \\ c_C \end{pmatrix} = M^{-1} \begin{pmatrix} \alpha \\ \beta \\ \gamma \end{pmatrix} \quad (12)$$

In column 7, line 21, please delete "1.".

UNITED STATES PATENT AND TRADEMARK OFFICE
CERTIFICATE OF CORRECTION

PATENT NO. : 4,914,719

DATED : April 3, 1990

INVENTOR(S) : Brendan Conlon et al.

It is certified that error appears in the above-identified patent and that said Letters Patent is hereby corrected as shown below:

In column 7, line 22, please start a new paragraph by inserting --1.-- before the first occurrence of "The ".

In column 7, line 28, please delete "2.".

In column 7, line 29, please start a new paragraph by inserting --2.-- before "For".

In column 7, between lines 34 and 35, please start a new paragraph beginning with "3."

In column 7, line 40, please delete "$\bar{D}\lambda 1, \bar{D}\lambda 2$" and substitute therefor $-- \bar{D}_{\lambda_1}, \bar{D}_{\lambda_2} --$ In column 7, between lines 41 and 42, please start a new paragraph beginning with "4."

In column 7, line 54, please delete IT and substitute therefor --I/T--.

In column 8, line 59, after "splitter" please insert --12--.

UNITED STATES PATENT AND TRADEMARK OFFICE
CERTIFICATE OF CORRECTION

PATENT NO. : 4,914,719

DATED : April 3, 1990

INVENTOR(S) : Brendan Conlon et al.

It is certified that error appears in the above-identified patent and that said Letters Patent is hereby corrected as shown below:

In column 11, line 12, please delete "greate" and substitute therefor --greater--.

Signed and Sealed this

Twenty-fourth Day of December, 1991

Attest:

HARRY F. MANBECK, JR.

*Attesting Officer*   *Commissioner of Patents and Trademarks*